United States Patent [19]

Larkins, Jr.

[11] 4,434,241

[45] Feb. 28, 1984

[54] CATALYST RECOVERY PROCESS FROM TAR FROM CARBONYLATION REACTIONS

[75] Inventor: Thomas H. Larkins, Jr., Kingsport, Tenn.

[73] Assignee: Eastman Kodak Company, Rochester, N.Y.

[21] Appl. No.: 424,727

[22] Filed: Sep. 27, 1982

[51] Int. Cl.³ .................. B01J 31/40; B01J 23/96; B01J 27/32; C07C 51/12
[52] U.S. Cl. .................................... 502/24; 260/549; 423/22; 423/179.5; 423/488; 423/504; 502/28
[58] Field of Search ............. 252/413, 412, 420, 416; 423/22, 179.5, 488, 504; 260/549

[56] References Cited

U.S. PATENT DOCUMENTS 4,241,219 12/1980 Wan ................................. 260/549
4,341,741 7/1982 Davidson et al. ..................... 423/22
4,388,217 6/1983 Hembre et al. ..................... 252/413

*Primary Examiner*—P. E. Konopka
*Attorney, Agent, or Firm*—David E. Cotey; Daniel B. Reece, III

[57] ABSTRACT

The present invention provides a process for the recovery of rhodium, lithium, and iodine values from tar which is generated during carbonylation reactions. The process comprises sequentially extracting the tar with water and then leaching the remaining tar with acetic acid, burning the resulting residue, and recycling the resulting rhodium-enriched residue to the reaction process. Preferably, the process further comprises the recovery of iodine values by the incineration of the acetic acid leachate and treatment of the off-gas with aqueous alkali hydroxide. Lithium values are recovered by evaporating water from the aqueous phase of the water extraction step and recycling the resulting residue to the reaction process.

4 Claims, No Drawings

CATALYST RECOVERY PROCESS FROM TAR FROM CARBONYLATION REACTIONS

DESCRIPTION

Background of the Invention

The present invention relates to a process for recovering rhodium, lithium, and iodine values from tar which is generated during carbonylation reactions. More particularly, the present invention is directed toward the recovery of catalyst values from tars formed during the preparation of acetic anhydride by the rhodium-catalyzed carbonylation of methyl acetate.

The use of catalyst systems comprising rhodium and an iodine compound in the preparation of acetic anhydride by the carbonylation of methyl acetate has been reported in the patent literature. See, for example, Belgian Patent No. 819,455, British Published Patent Application 2,013,184, Japanese Published Patent Applications Nos. 75-47921 and 75-47922, and U.S. Pat. Nos. 3,927,078 and 4,046,807. Those publications also disclose that the reaction rate can be increased if the catalyst system contains a promoter such as certain amines, phosphines, and inorganic materials such as lithium compounds. The use of amines and phosphines, particularly under conditions giving high space-time yields, causes formation of tars which cannot be handled in a continuous process. The use of lithium compounds, such as lithium iodide or lithium acetate, does not entirely avoid the formation of tar, but the tar that is formed is not unmanageable.

Tar formation, which is essentially unavoidable in the carbonylation of methyl acetate, increases as reaction conditions, such as temperature and pressure, are increased to obtain a desirably high space-time yield, e.g., 400 g/l-hr or greater. It is known (U.S. Pat. No. 4,046,807) that the inclusion of hydrogen in the gas feed to the carbonylation reactor in a system employing triphenylphosphine can suppress, but still not completely avoid, tar formation. If not removed from the reaction system, tar will increase to the point where catalyst activity is greatly diminished, eventually resulting in the termination of the carbonylation reaction.

Because of the cost of rhodium, high efficiency catalyst recycling in the rhodium-catalyzed carbonylation of methyl acetate is of extreme importance for the successful operation of an acetic anhydride process. A survey of the literature on recovery/recycling procedures for rhodium species from reaction mixtures reveals a variety of methods relying on selective reduction and deposition of rhodium metal from these mixtures (Published German Patent Application No. 2,263,852; Japanese Published Patent Application No. 77-045-425) or simply oxidation/incineration of the tar materials to volatile species and collection of the nonvolatile Rh/Rh$_2$O$_3$ remains (U.S. Pat. Nos. 3,920,449 and 4,135,911). In such high temperature incineration processes for the recovery of rhodium values, rhodium losses can occur due to the formation at high temperatures of volatile rhodium-containing compounds and/or the entrainment of rhodium-containing ash in the combustion gases.

U.S. Pat. No. 4,340,570 further discloses that rhodium values can be freed from tar residues by a series of treatments with amines and other reagents, thereby enabling the rhodium to be extracted by subsequent contact with an aqueous halogen acid. U.S. Pat. No. 4,340,569 discloses that the effect of such amine treatments can be improved by pretreatment of the residues with alkanols.

In the methyl acetate carbonylation process, the catalytically active form of rhodium has been identified as the anion $[Rh(CO)_2I_2]^-$. This knowledge coupled with the expectation that tar formed in the process will be largely hydrocarbon in nature suggested that aqueous extraction might be a viable technique for the separation of rhodium values from anhydride tar by-products. It has further been disclosed that soluble rhodium species can be stabilized during aqueous extraction of tars by the inclusion of HI in the water used as the extraction medium (see commonly-assigned U.S. patent application Ser. No. 304,773). Commonly-assigned U.S. patent application Ser. No. 381,275 further discloses that residual rhodium contained in the tar which has been subjected to an aqueous HI extraction can be recovered by extracting a solution of the tar with aqueous ammonia.

U.S. Pat. No. 3,887,489 discloses a process for the regeneration of a spent catalyst solution wherein the solution is heated with agitation at about 100° to 190° C. at a pressure sufficient to boil the solution for a period of time necessary to obtain a rhodium-containing precipitate from the solution. A solvent selected from water, acetic acid, and mixtures thereof and an iodine-containing component are added to the rhodium-containing precipitate and the resulting mixture is heated in contact with carbon monoxide until solution is effected.

Despite the numerous attempts in the art to provide processes for the recovery of rhodium catalyst values, the need for an effective, efficient, and facile process remained. The present invention now provides such a process for the recovery of rhodium, lithium, and iodine values from carbonylation residues. The process comprises a unique sequence of discrete steps which has not hitherto been disclosed in the art.

SUMMARY OF THE INVENTION

The present invention provides a process for the recovery of rhodium, lithium, and iodine values from tar which is generated during carbonylation reactions. The process comprises the steps of:

(a) vaporizing volatile components from the tar;

(b) adding water to the remaining tar and heating the resulting mixture so as to extract corrosion metal ions and lithium ions into the aqueous phase;

(c) separating the aqueous phase;

(d) drying the resulting tar residue and leaching the residue with hot acetic acid so as to remove iodine species, soluble organic polymers, and corrosion metal ions from the residue;

(e) burning the residue at a temperature and for a period of time sufficient to remove carbonaceous impurities therefrom; and (f) recycling the rhodium-enriched residue to the reaction process.

DETAILED DESCRIPTION OF THE INVENTION

The present invention provides a process for the treatment of tarry residues which are produced during carbonylation reactions and for the recovery of catalyst values therefrom. While the present process is directed particularly to the recovery of catalyst values from the carbonylation of methyl acetate to acetic anhydride, the present process is not limited to that particular reaction process. It is contemplated that the present process can be used in conjunction with rhodium-catalyzed carbonylation reactions in general.

Typically, the tarry residues which are produced during carbonylation reactions are removed continuously or intermittently from the carbonylation system in the form of a solution in a mixture of the compounds present in the system. The catalyst-tar solution may be removed either directly from the reactor or, in the case of a system employing a liquid product take-off from the reactor, from some point in the normal catalyst recycle stream.

The process with which the present invention is particularly concerned comprises the preparation at elevated pressure and temperature of acetic anhydride by the liquid phase reaction of methyl acetate and carbon monoxide in the presence of rhodium, an iodine compound (such as methyl iodide), and a lithium compound. In such a process, a feed mixture containing methyl acetate is continuously fed to a carbonylation reactor and a reaction mixture containing acetic anhydride is continuously removed. Optionally, up to about 7 volume percent of the carbon monoxide gas employed may consist of hydrogen. In the practice of the process, the feed to the reactor is such as to maintain within the reaction mixture (1) about 250 to 1300 ppm, preferably about 500 to 1000 ppm, rhodium, (2) about 175 to 5000 ppm, preferably about 1500 to 3700 ppm, lithium, and (3) about 7 to 35 weight percent methyl iodide. The remainder of the reactor contents consists mostly of methyl acetate reactant and acetic anhydride product with minor amounts of by-products such as ethylidene diacetate and acetone. The reactor feed optionally may contain a solvent such as acetic acid, e.g., in an amount that will maintain about 5 to 40 weight percent acetic acid in the reaction mixture. In a liquid take-off system, the catalyst components, i.e., the rhodium, lithium, and iodine as methyl iodide, are recovered from the reactor effluent and are recycled. When necessary, fresh rhodium, as rhodium chloride, rhodium acetate, or other rhodium containing compound, and lithium, as lithium hydroxide, lithium iodide, lithium acetate, or other lithium-containing compound are added to the catalyst recycle. The fresh rhodium and lithium can be conveniently added as a solution in acetic acid. When the iodine needs to be supplemented, it may be added to the system as iodine ($I_2$), as methyl iodide, or, at least in part, as lithium iodide. In a vapor take-off system, all or essentially all of the rhodium and lithium catalyst components remain in the reactor and, thus, the risk of their depletion from the process is reduced considerably.

The tar material formed in the process has very reproducible, but poorly resolved, spectral features. These features appear in tars formed in both liquid and vapor take-off processes and in runs with both high and low tar formation rates.

From the combined information of IR, H NMR, C NMR, and elemental analysis, certain aspects of the "structure" may be proposed. However, the poor resolution in the H and C NMR spectra thwart hopes for absolute identification and are suggestive of a highly amorphous material. The C NMR shows two major broad band absorptions of approximately equal intensity, one in the alkyl region (13-45$\delta$) and the other in the aromatic region (120-140$\delta$). For the same material, the H NMR shows almost no aromatic protons relative to the alkyl bands at 0.9-1.7 and 1.6-3.0$\delta$. In combination, these two spectra, therefore, suggest a polyalkylated aromatic material substituted to the exclusion of aromatic protons. Additionally, the C NMR shows some very minor absorptions assignable to carbonyl moieties, a feature strongly suggested by the IR band at 1700 cm$^{-1}$. The IR also suggests carbon-oxygen (1180 cm$^{-1}$) and oxygen-hydrogen (36-3300 cm$^{-1}$) bonds. The elemental analysis substantiates the expectations of aromatic unsaturation showing 0.60 unsaturations per carbon and an empirical formula of $C_{36}H_{41}O_4I_{0.15}$. Despite the ambiguities of actual tar structure, more practical considerations include the observations that the tar is readily soluble in organic solvents and has proven amenable to liquid/liquid extraction.

According to the process of the present invention, the tar-containing reaction mixture which is obtained from the carbonylation reaction process is subjected to a stripping operation so as to vaporize volatile components from the tar. The volatile components which are removed from the tar are those having a boiling point less than about 175° C. under a vacuum of about 100 mm Hg. Of course, other suitable conditions of temperature and pressure for removing such components are apparent to those of ordinary skill in the art.

After the volatile components have been removed from the initial tar-containing reaction mixture, water is added to the remaining tar and the resulting mixture is heated so as to extract corrosion metal ions and lithium ions into the aqueous phase. Ordinarily, the water is added in an amount of about 5 to 10 parts of water to 1 part of the tar (unless otherwise noted, the term "part" as used herein denotes parts by weight). The resulting mixture is heated to reflux temperature and is maintained at that temperature for a period of time of about 30 minutes to 1 hour or for any other period of time which is sufficient to extract corrosion metal ions and lithium ions into the aqueous phase. The water-tar mixture is then cooled to about room temperature, and the solids which remain are collected, e.g., by filtration. Such solids will be the organic tarry residue remaining after the water extraction. The solids are washed thoroughly with water, and the wash water is combined with the aqueous filtrate.

The combined aqueous phase resulting from the water extraction step contains lithium values and small amounts of corrosion metal ions which can be recycled to the reaction process. In preferred embodiments, therefore, the aqueous phase is concentrated by the evaporation of water, and the residue, containing lithium catalyst values, is recycled to the reaction process. The evaporated water is discarded as waste.

The solids which were recovered from the water extraction step represent the remainder of the initial tar and contain rhodium and iodine values yet to be recovered. In order to recover the additional catalyst values, the solids are dried at suitable elevated temperatures (e.g., about 60°-90° C., preferably, about 80° C.). The dry solids are then leached with hot acetic acid. While it is conceivable that other alkanoic acids, such as propionic acid, could also be used, other alkanoic acids would present purification and separation difficulties which are not encountered with the use of acetic acid, which is already employed in the system as a solvent for the carbonylation reaction. The acetic acid is advantageously employed in an amount of about 5 to 20 parts by weight of acetic acid to 1 part of dry solids. Preferably, the acetic acid is employed in an amount of about 10 parts acetic acid to 1 part dry solids. The solids are leached with the acetic acid at reflux temperature for a period of time sufficient to remove iodine species, soluble organic polymers, and corrosion metal ions from the tar residue. Typically, the solid tar residue is leached at reflux temperature for a period of time of about 4 to 6 hours. The acetic acid/solids mixture is then cooled to room temperature, and the solids are collected, for example, by filtration through a fine filter.

The solids which remain represent the rhodium-enriched tar residue. However, in addition to rhodium species, this residue contains large amounts of carbonaceous impurities. Therefore, the residue is burned at a temperature and for a period of time sufficient to remove carbonaceous impurities therefrom. Typically, this residue is burned at temperatures of about 400° to 600° C. for periods of time of about 2 to 10 hours in order to remove maximum amounts of carbonaceous impurities. This incineration step leaves behind a small amount of rhodium-rich (e.g., 60% rhodium or more) residue. This rhodium-enriched residue is then recycled to the reaction process.

The acetic acid filtrate remaining from the leaching step contains useful iodine values which also can be recovered. The recovery of the iodine values is accomplished by evaporating the acetic acid from the filtrate and then roasting the residues in air. The acetic acid which is stripped from the filtrate can be recycled to the reaction process as solvent. The off-gases are scrubbed with aqueous alkali hydroxide or mixed alkali hydroxide-alkali iodide solution in order to recover the iodine values contained therein. Sulfuric acid is then added to the resulting iodide-containing alkali hydroxide solution. The resulting sulfuric acid solution is then heated at a temperature and for a period of time sufficient to distill hydrogen iodide and iodine from the sulfuric acid solution. These iodines values are recovered and recycled to the reaction process. This sulfuric acid treatment is known technology which would be available to one of ordinary skill in the art.

This invention will be further illustrated by the following Examples although it will be understood that the Examples are included merely for purposes of illustration and are not intended to limit the scope of the invention.

EXAMPLE 1

Acetic anhydride reactor heel (205 g) was stripped on a rotary evaporator under about 100 mm mercury pressure with an oil bath temperature of 150° C. until volatiles were no longer being removed. About 700 ml water was then added to the tar-like residue from the vacuum stripping operation, and the mixture was heated at reflux for eight hours, cooled, and vacuum filtered. The solid residue was washed several times, and the wash water was combined with the filtrate from the water extraction to give a total volume of 955 ml. The remaining solids were dried on a steam bath to give 4.95 g dried solids. The dried solids contained 752 ppm Li, 212 ppm Ni, 2.13% Fe, 0.23% Cr, 3.5% Rh, and 852 ppm Mo. The combined filtrate and wash contained 0.15% Li, 1.5 ppm Ni, 59.5 ppm Fe, 28 ppm Cr, 3 ppm Rh, and less than 0.2% ppm Mo.

EXAMPLE 2

A sold material (5.4 g) was prepared as described in Example 1. This solid material contained 3.24% rhodium, 220 ppm Mo, 74 ppm Ni, 0.29% Fe, 883 ppm Cr, and 0.22% Li. This solid material was extracted for eight hours at reflux with about 150 ml acetic acid in a Soxhlet extractor. The mixture was cooled overnight and was then filtered under gravity through Whatman No. 42 filter paper, and the solid was washed on the filter with a small amount of acetic acid. The combined volume of the filtrate and the wash acid was 195 ml. The filtrate contained no rhodium when analyzed by atomic absorption. The filter paper and Soxhlet thimble, and the solids contained thereon, were burned at 550° C. under air for eight hours in a muffle furnace. After incineration, 0.27 g residue remained. The residue contained 62.09% rhodium, 1.55% Fe, 406 ppm Ni, 0.67% Cr. 0.41% Li, and 0.28% Mo. The residue contained 95.8% of the rhodium which had been contained in the initial solid material subjected to acetic acid leaching.

Thus, the present invention provides an efficient and effective process for the recovery of rhodium values from carbonylation reaction processes.

While the invention has been described in detail with particular reference to preferred embodiments thereof, it will be understood that variations and modifications can be effected within the spirit and scope of the invention.

I claim:

1. A process for the recovery of rhodium, lithium, and iodine values from tar which is generated during carbonylation reactions comprising the steps of:
   (a) vaporizing volatile components from said tar;
   (b) adding water to the remaining tar and heating the resulting mixture so as to extract corrosion metal ions and lithium ions into the aqueous phase;
   (c) separating said aqueous phase;
   (d) drying the resulting tar residue and leaching said residue with acetic acid at reflux temperature so as to remove iodine species, soluble organic polymers, and corrosion metal ions from said residue;
   (e) burning said residue at a temperature and for a period of time sufficient to remove carbonaceous impurities therefrom; and
   (f) recycling the rhodium-enriched residue to the reaction process.

2. The process of claim 1 which comprises the additional steps of concentrating the acetic acid leachate and burning the resulting concentrate; scrubbing the off-gas from said burning step with aqueous alkali hydroxide; adding sulfuric acid to the resulting iodide-containing alkali hydroxide solution; and heating the resulting sulfuric acid solution so as to distill and recover $HI/I_2$.

3. The process of claim 1 which comprises the additional steps of evaporating water from the aqueous phase of the water extraction step and recycling the resulting residue to the reaction process.

4. A process for the recovery of rhodium, lithium, and iodine values from tar which is generated durin the carbonylation of methyl acetate to acetic anhydride comprising the steps of:
   (a) vaporizing volatile components from said tar;
   (b) adding water to the remaining tar and heating the resulting mixture so as to extract corrosion metal ions and lithium ions into the aqueous phase;
   (c) separating said aqueous phase;
   (d) evaporating water from said aqueous phase and recycling the resulting lithium-rich residue to the reaction process;
   (e) drying the tar residue from the water extraction step and leaching said residue with acetic acid at reflux temperature so as to remove iodine species, soluble organic polymers, and corrosion metal ions from said residue;

(f) burning said residue at a temperature and for a period of time sufficient to remove carbonaceous impurities therefrom;

(g) recycling the rhodium-enriched residue to the reaction process;

(h) concentrating the acetic acid leachate and burning the resulting concentrate;

(i) scrubbing the off-gas from said burning step with aqueous alkali hydroxide;

(j) adding sulfuric acid to the resulting iodide-containing alkali hydroxide solution; and (k) heating the resulting sulfuric acid solution so as to distill and recover $HI/I_2$.

* * * * *